(12) United States Patent
Sridharan et al.

(10) Patent No.: US 9,399,771 B2
(45) Date of Patent: Jul. 26, 2016

(54) METHODS AND COMPOSITIONS FOR HIGH EFFICIENCY TRANSFECTION OF SIRNA

(71) Applicants: Arati Sridharan, Chandler, AZ (US); Jitendran Muthuswamy, Chandler, AZ (US)

(72) Inventors: Arati Sridharan, Chandler, AZ (US); Jitendran Muthuswamy, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 48 days.

(21) Appl. No.: 14/036,426

(22) Filed: Sep. 25, 2013

(65) Prior Publication Data

US 2014/0106429 A1 Apr. 17, 2014

Related U.S. Application Data

(60) Provisional application No. 61/713,310, filed on Oct. 12, 2012.

(51) Int. Cl.
*C12N 13/00* (2006.01)
*C12N 15/11* (2006.01)

(52) U.S. Cl.
CPC .............. *C12N 13/00* (2013.01); *C12N 15/111* (2013.01); *C12N 2310/14* (2013.01); *C12N 2320/32* (2013.01)

(58) Field of Classification Search
None
See application file for complete search history.

(56) References Cited

U.S. PATENT DOCUMENTS 4,946,793 A * 8/1990 Marshall, III ............... 435/285.2
2009/0053813 A1 * 2/2009 Evans ........................... 435/461

OTHER PUBLICATIONS

Jain et al. "Bio-chip for spatially controlled transfection of nucleic acid payloads into cells in a culture" Lab Chip 7: 1004-1011, 2007.*
Belting et al. "Developments in macromolecular drug delivery", Methods in Molecular Biology, edited by Belting 480: 1-10, 2009.*
Fujimoto et al. "Electroporation microarray for parallel transfer of small interfering RNA into mammalian cells." Analytical and Bioanalytical Chemistry 392(7-8): 1309-1316, 2008.*
Qiagen "HiPerFect Transfection Reagent Handbook", Fifth edition, available from company's webpage, (www.qiagen.com), May 2008.*
Jain et al. "Microsystem for transfection of exogenous molecules with spatio-temporal control into adherent cells" Science direct—Biosensors and Bioelectronics 22: 863-870 (2007).
Patel et al. "High efficiency, Site-specific Transfection of Adherent Cells with siRNA Using Microelectrode Arrays (MEA)" J. Vis. Exp. (67), e4415 10.3791/4415, DOI : 10.3791/4415 (2012).
Sridharan et al. "Voltage Preconditioning Allows Modulated Gene Expression in Neurons Using PEI-complexed siRNA" Molecular Therapy-Nucleic Acids, 2, e82 (2013).

* cited by examiner

*Primary Examiner* — Emily Cordas
(74) *Attorney, Agent, or Firm* — Quarles & Brady LLP

(57) ABSTRACT

Described herein are methods and compositions for high efficiency transfection of siRNA into a cell population. Such methods and compositions utilize a low voltage pre-conditioning pulse to modulate the efficiency of siRNA transfection. In some embodiments, the methods and compositions permit spatial and temporal control of siRNA transfection efficiency within a population of cells. The disclosed methods and compositions, in some embodiments, are amenable to high throughput applications such as siRNA library-based phenotypic screening.

11 Claims, 16 Drawing Sheets

METHODS AND COMPOSITIONS FOR HIGH EFFICIENCY TRANSFECTION OF SIRNA

CROSS REFERENCES TO RELATED APPLICATIONS

This patent application claims priority to U.S. provisional patent application No. 61/713,310, filed on Oct. 12, 2012, which is incorporated by reference herein in its entirety.

BACKGROUND

Non-viral transfection methods are increasingly used in both in vitro and in vivo systems for siRNA delivery. However, they have mixed results in difficult-to-transfect cells such as primary neuronal cells where chemical transfection typically yields can vary from 3-30% efficiency. Although multiple alternate transfection systems have made major strides, all have significant trade-off issues between transfection efficiency and viability. Thus, there is a continuing need for non-viral siRNA transfection methods and compositions that offer high transfection efficiency with little loss in cell viability, especially in typically difficult to transfect cell types.

BRIEF SUMMARY

Described herein are methods, compositions, and systems for high efficiency siRNA transfection based on the unexpected finding that combining electric field pre-conditioning of cells with chemical transfection agent greatly enhances siRNA transfection relative to chemical transfection alone while leaving cell viability virtually unaffected.

Accordingly, in one aspect described herein is a high efficiency siRNA transfection method comprising the steps of (i) subjecting a population of cells adhering on an electrically conductive cell culture surface to one or more low voltage pulses in a range of about −3 V to about +3 V; and (ii) transfecting siRNA, using a transfection agent, into the population following the one or more low voltage pulses to obtain a transfected population of viable cells, wherein the one or more low voltage pulses provide a voltage from about −3 V to about −0.2 V. In some embodiments, the cells to be transfected include primary cells (e.g., neurons). In other embodiments, the cells to be transfected are from a neuronal cell line (e.g., a neuroblastoma cell line). In one embodiment, the cells to be transfected are Neuro2a neuroblastoma cells.

In some embodiments of the above-mentioned method, the electrically conductive cell culture surface on which the cells to be transfected are cultured includes indium tin oxide (ITO).

In some embodiments, the population of cells to be transfected is less than about 80% confluent during the transfection step. In other embodiments, the population of cells to be transfected is subjected to at least three low voltage pulses. In one embodiment, the one or more low voltage pulses provide a voltage of about −1 V. In some embodiments, the one or more low voltage pulses has a width of about 1 msec to about 100 msec.

In some embodiments, the electrically conductive cell culture surface to be used is provided in the form of one or more microelectrodes (e.g., two microelectrodes). In some embodiments, the electrically conductive cell culture surface is provided as a microelectrode array.

In some embodiments, the one or more low voltage pulses comprises at least one negative voltage pulse and one positive voltage pulse.

In some embodiments, the transfection agent for the above-mentioned method contains polyethyleneimine (PEI).

In another aspect described herein is a high efficiency siRNA transfection kit that includes: (i) a cell culture vessel comprising an electrically conductive cell culture surface; and (ii) a transfection agent suitable for siRNA transfection, wherein the transfection agent is substantially free of nanoparticles.

In some embodiments, the high efficiency siRNA transfection kit includes a transfection agent that contains polyethyleneimine.

In some embodiments, the electrically conductive cell culture surface, included in the above-mentioned high efficiency siRNA transfection kit, contains indium tin oxide. In other embodiments, the kit also contains a population of cells cultured on the conductive cell culture surface.

In some embodiments, the high efficiency siRNA transfection kit also includes one or more siRNAs directed against one or more genes expressed in a population of cells to be transfected.

In yet another aspect provided herein is a high efficiency siRNA transfection system that includes: (i) a cell culture vessel comprising cells in a pre-conditioning buffer and adhering to an electrically conductive surface; (ii) a voltage pulse generator operably coupled to the cell culture vessel; and a cationic transfection agent-siRNA complex within the cell culture vessel, wherein the transfection agent is substantially free of nanoparticles.

In some embodiments, the high efficiency siRNA transfection system includes an electrically conductive surface that contains indium tin oxide. In some embodiments, the cell culture vessel is a multiwell cell culture plate comprising at least 24 wells to 1536 wells. In some embodiments, the cultured cells contained in the high efficiency siRNA transfection system include primary cells. In one embodiment, the primary cells to be transfected are neurons.

In some embodiments, the voltage pulse generator included in the high efficiency siRNA transfection system is configured to provide one or more voltage pulses from about −3V to about +3V.

In a further aspect provided herein is a method for spatial and temporal modulation of siRNA transfection, comprising the steps of:
(i) Providing a population of cells cultured on a shared microelectrode array;
(ii) subjecting a first subpopulation of cells growing on or near a first subset of microelectrodes in the microelectrode array to one or more negative, low voltage pulses through the first subset of microelectrodes; and subjecting a second subpopulation of cells growing on or near a second subset of microelectrodes in the microelectrode array to one or more positive, low voltage pulses through the second subset of microelectrodes; and
(iii) contacting the population of cells, following the negative and positive low voltage pulses, with a transfection agent, and at least one siRNA; wherein the first subpopulation is transfected with a greater efficiency than that of the second subpopulation.

In some embodiments of the method for spatial and temporal modulation of siRNA transfection, the method includes the additional steps of (iv) removing the at least one siRNA and transfection agent from contact with the population of cells after step (iii); (v) providing negative and positive voltage low voltage pulses from a different subset of microelectrodes than the subset used in step (ii); and (vi) contacting the population of cells with a transfection agent at least one siRNA that is different from the at least one siRNA in step (iii); wherein a subpopulation of cells different from the subpopulation

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein.

Figure 1:
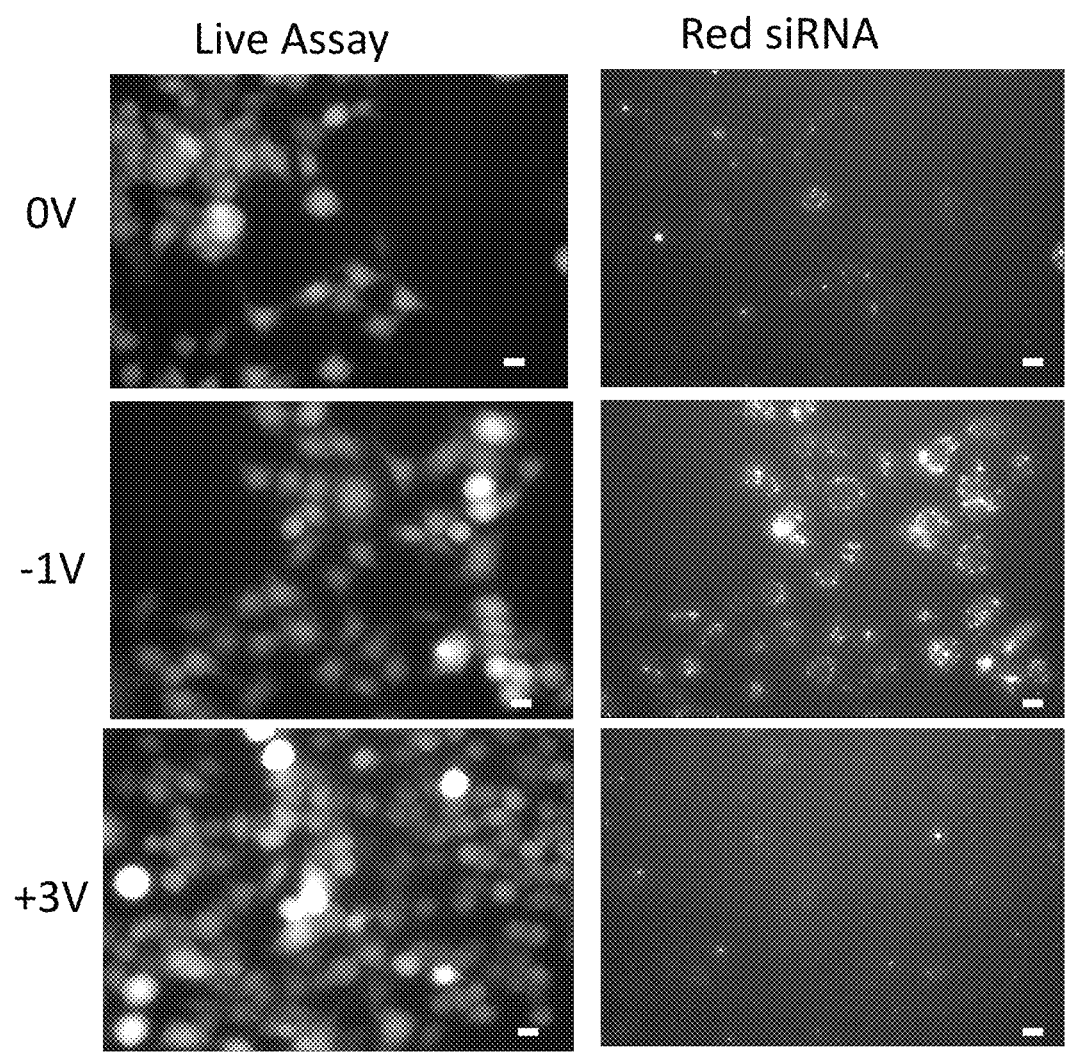
FIG. 1 shows fluorescence images from a standard live assay of calcein-AM (images in left column) and ALEXA FLUOR® labeled siRNA uptake (images in right column) conducted on transfected neuro2a cells preconditioned with different voltages. Transfection efficiencies were 62%±14% (0 V), 98%±3.8% (−1 V), and 37%±7.5% (+3 V) of live cells, which were the majority of cells in all cases. The distribution of fluorescent siRNA intensities after pre-conditioning with −1 V was more uniform throughout the cell compared with those at 0 or 3 V, suggesting higher cellular uptake at −1 V. Bar indicates 50 µm.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

Figure 15:
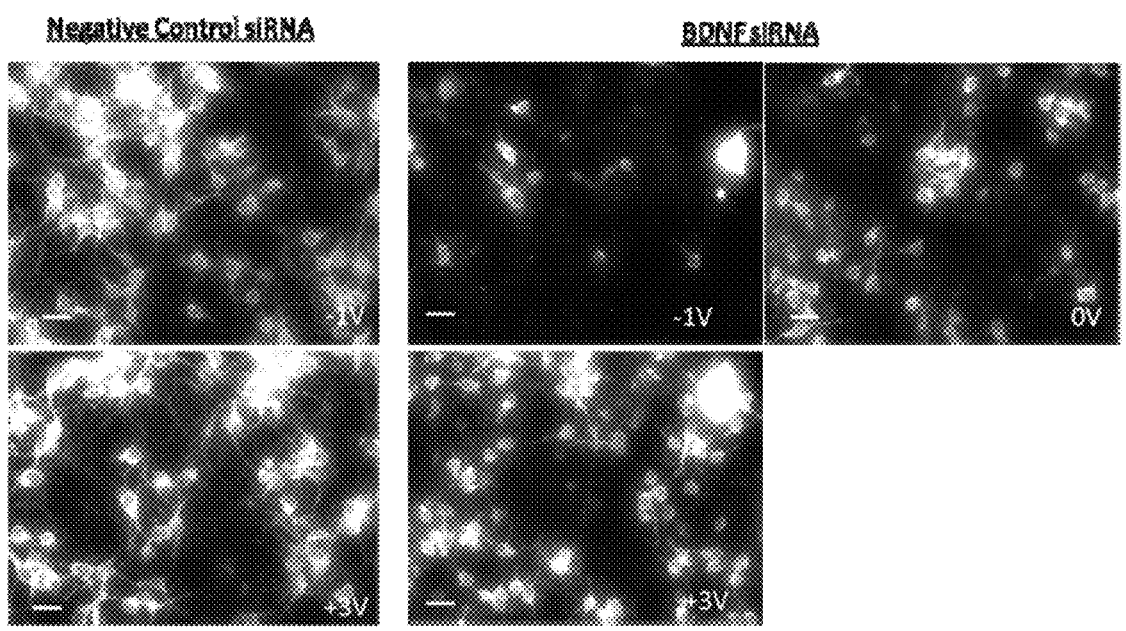

FIG. 15 shows a series of MAP2 immunofluorescence images from cultured hippocampal neurons transfected with shRNA against Brain Derived Neurotrophic Factor (BDNF) or a negative-control siRNA, and fixed 24 hours post-transfection. Transfections were performed with positive or negative voltage pulses of varying amplitude as indicated. were taken at 24 hours after transfection. Neurite loss and on-target cytotoxicity are associated with increasing level of BDNF siRNA transfection. Note the lower level of transfection observed at +3V than at 0V. Bar represents 50 μm.

Figure 16:
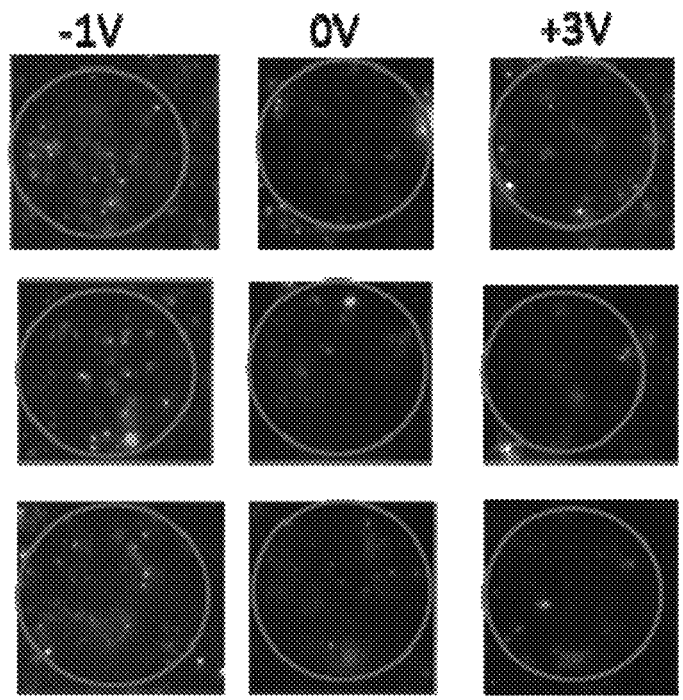
Figure 16:
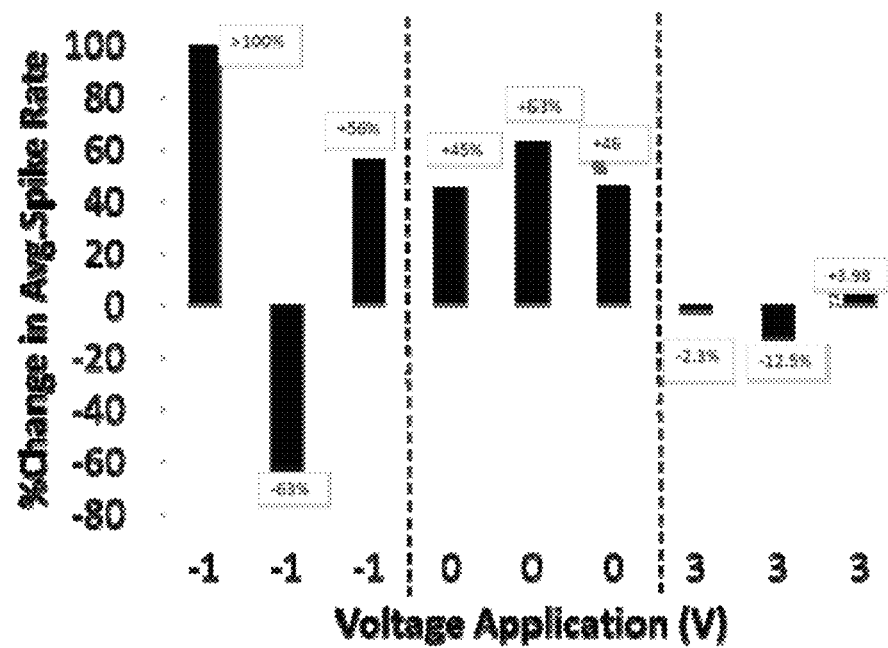

FIG. 16 (A) shows a fluorescence image of BACE1 siRNAs co-transfected with fluorescently labeled negative control siRNAs into DIV primary hippocampal neurons grown on a multielectrode array (indicated by the circles). Varying pre-conditioning pulses were provided from different sets of microelectrodes within the array as indicated. Increased uptake is seen in −1V electrodes compared to 0V and +3V similar to the macroscale methods previously described. Panel (B) shows the functional effect of BACE1 siRNA transfection on the average spike rate in the hippocampal neurons one hour post-transfection. Note the position-dependent effect based on the voltage pulse characteristics provided at the varying microelectrode positions.

DETAILED DESCRIPTION

Disclosed herein is are methods, kits, systems, and compositions for high efficiency transfection of siRNA based on the unexpected finding that the application of a low voltage pulse to ("voltage pre-conditioning") greatly enhances, in a synergistic manner, siRNA transfection of cells by a chemical transfection agent ("transfection agent") such as polyethyleneimine (PEI). The majority of electric field assisted transfection reported in the past involved electroporation, where high electric field intensities (0.5-10 kV/cm) are applied to reversibly permeabilize the membrane and allow naked siRNA or DNA into the cell. Large-scale, high-voltage electroporation typically yields 20-30% efficiency with a large decrease in viability. In contrast, the disclosed siRNA transfection methods and compositions provide great advantages compared to many conventional transfection methods, as those disclosed herein have very low impact on cell viability, are minimally affected by cell density during transfection, and allow a graded level of gene expression inhibition depending on the amount of siRNA transfected. While not wishing to be bound by theory, it is believed that this effect occurs, at least in part, through the enhancement of an active cellular uptake process such as endocytosis.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, the preferred methods and materials are described herein.

I. DEFINITIONS

In describing the embodiments and claiming the invention, the following terminology will be used in accordance with the definitions set out below.

As used herein, "about" means within 5% of a stated range within the relevant parameter.

As used herein, "siRNA" or "siRNAs" refer to short interfering RNA or silencing RNA, a class of double-stranded RNA molecules, 20-25 nucleotides in length.

As used herein, "electrically conductive" means able to support delivery of a voltage pulse of specified characteristics.

II. METHODS

Described herein are methods for high efficiency transfection of siRNA into a population of cells. In various embodiments, the method includes subjecting a population of adherent cells cultured on an electrically conductive surface to one or more low voltage pulses in the range of about −3 V to about −0.2 V, and subsequently transfecting siRNA, following the voltage pulses into the cultured cell population using a transfection agent into the cultured cell population following the one or more low voltage pulses. While siRNAs are typically used in the presently disclosed methods and compositions, it should be understood that nucleic acids with similar physical-chemical characteristics, e.g., micro-RNAs (miRNAs) can also be used in the transfection methods and compositions described herein.

A wide range of cell types are suitable for use in the disclosed siRNA transfection methods. In some cases, the population of cells to be transfected include primary mammalian cells. Suitable types of primary mammalian cells include, but are not limited to, neurons, glia (e.g., astrocytes), neural progenitors, cardiomyocytes, myocytes, immune cells, hepatocytes, epithelial cells, adipocytes, and any combinations thereof. In some cases, the cells to be used are human cells. In other cases the cells are of non-human origin, e.g., from mice, rats, or non-human primates.

In some embodiments, the cells to be transfected are cells from a cell line. Examples of cell lines suitable for the methods described herein include, but are not limited to, neuro2A cells, neuroblastoma cell lines, Jurkat cells, PC12 cells, CHO cells, and pluripotent stem cells (e.g., human ES cells and human iPS cells). Methods for culturing the various cell types are known in the art and suitable for use with the present methods.

In various embodiments, the cell culture substrates to be used include an electrically conductive cell culture surface that allows a voltage pulse to be administered to an adherent population of cells. Suitable electrically conductive cell culture surface materials include, but are not limited to, indium tin oxide, gold, platinum, iridium, or a combination thereof. Such materials may be mounted on a solid cell culture material, e.g., glass, or cell culture plastic. In some embodiments, the electrically conductive cell culture surface material contains indium tin oxide. In some embodiments, the electrically conductive cell culture surface material, including electrodes, is substantially transparent. Optionally, the cell culture substrate may also include coating materials that support proliferation, differentiation, and/or viability of cells grown on the cell culture insofar as these materials do not impact the ability of the electrically conductive cell culture surface material to deliver a voltage pulse to adherent cells by more than about 10% relative to the desired voltage pulse value. One of ordinary skill in the art will appreciate that such cell culture coating materials are selected based on the types of cells to be grown. Examples of such coatings include, but are not limited to, polylysine, polyornithine, laminin, fibronectin, collagen, N-cadherin, Matrigel®, or a combination thereof.

Cell confluence at the time of transfection by the methods described herein may be varied, and can range from about 30% confluent to about 100% confluent, e.g. 30%, 35%, 40%, 45%, 50%, 55%, 60%, 65%, 70%, 80%, 85%, 95%, 97%, or another percentage of confluence from about 30% confluent to about 100% confluent.

Preferably, prior to applying one or more pre-conditioning voltage pulses to the population of cells to be transfected, the cell culture medium in which the cells have been grown is replaced with a pre-conditioning buffer, which, in some embodiments, is a simple buffer having a pH about 6.8 to 7.6 that is isotonic and having an ionic strength that is within the physiological range. Examples of suitable pre-conditioning buffers include, but are not limited to, phosphate-buffered saline (PBS) without calcium/magnesium, Hanks Balanced Salt Solution (HBSS), Ringer's Balanced Salt Solution, Tris-Buffered Saline, Normal saline, and the like. Once cells are in a pre-conditioning buffer, one or more square wave voltage pulses are administered to the population of cells for pre-conditioning. In some embodiments, the voltage of the one or more voltage pulses ranges from about −3 V to about −0.2 V, e.g., about −2.7 V, −2.2 V, −2.0 V, −1.8 V, −1.5 V, −1.3 V, −1.0 V, −0.8V, −0.6, V, −0.3 V, or another voltage from about −3 V to about −0.2 V. In some embodiments, the one or more voltage pulses are −1.0 V pulses.

In some embodiments, particularly where fine spatial control of siRNA transfection within a subpopulation of adherent cells is desired, the methods may include one or more positive voltage pulses, which actually provide a reduced transfection rate compared to transfection with a transfection agent (e.g., PEI) alone within the effective radius of the positive voltage pulse. Thus, for example, in embodiments that allow control of individual microelectrodes within a region of interest, microelectrodes at desired positions on a cell culture surface provide a negative voltage pre-conditioning pulse to enhance transfection by the transfection agent, whereas other microelectrodes at desired positions on the cell culture surface provide a positive voltage pre-conditioning pulse, that actively prevents the transfection agent from delivering siRNA within the vicinity of the positive voltage pre-conditioning microelectrode. Such a configuration allows the transfection of cells grown on the same surface with a desired spatial pattern. For example, if one wished to evaluate the effect of an siRNA to affect the ability of a first population of cells grown on a cell culture surface to innervate a second set of cells grown on a separate region of the cell culture surface, but wanted to selectively examine the effect of the siRNA on the first cell population, spatial control of the voltage-prepulse conditioning would allow selective transfection of the first cell population.

In some embodiments, a subset of cells within a cell population is transfected by applying a first spatial pattern of microelectrode-provided negative and positive voltage pulses to introduce a first set of siRNAs into the first cell population in the presence of a transfection agent (e.g., PEI). Subsequently, at least a second spatial pattern of microelectrode-provided negative and positive voltage pre-conditioning pulses is provided to stimulate transfection in a second subpopulation of cells according to the second spatial pattern of negative and positive pre-conditioning voltage pulses. In some embodiments, prior to a second "transfection spatial pattern," the first set of siRNAs is washed out, and a second set of siRNAs is added along with a transfection agent following or during the second transfection spatial pattern. As a result, within the same culture subpopulations of the cells are transfected with distinct siRNAs. For convenience, in some embodiments, each set of siRNAs can be labeled with a distinct fluorescent dye, such that subpopulations of cells transfected with different siRNAs will be distinctly labeled.

In some embodiments, the level of siRNA transfection within a population of cells to be transfected is modulated, i.e., "dosed" by varying both the voltage pulse amplitudes and voltage pulse signs. For example, in some cases, two positive voltage pulses are followed by a single negative voltage pulse, which gives a lower "dose" of siRNA transfection compared to, e.g., a single negative voltage pulse alone, or two negative voltage pulses alone, etc. . . . . .

In some embodiments, sequential, combinatorial use of voltage pulse pre-conditioning spatial patterns with different combinations of siRNAs allows transfection of subpopulations of cells with overlapping or completely different sets of siRNAs. Beyond these exemplary embodiments, those of ordinary skill in the art will appreciate that there are many other applications e.g., co-culture applications where spatial control of transfection is desired and enabled by the methods described herein. In some embodiments, where a positive voltage pulse is provided, the positive pulse voltage ranges from about +0.2 V to about +3 V, e.g., about 0.3 V, 0.6 V, 0.8 V, 1.0V, 1.3 V, 1.5 V, 1.8 V, 2.0 V, 2.7 V, or another positive voltage range from about +0.2V to about +3.0 V.

In some embodiments, the methods provided herein are used in a high-throughput format in which an array of microelectrodes is used where each microelectrode in the array is provided in small or microwell which contains a distinct siRNA or a distinct set of siRNAs. This format is very useful, for example, in conducting whole genome siRNA screens in primary cells, e.g., in human neurons.

The number of voltage pulses administered during the pre-conditioning step of the transfection methods described herein can range from 1 to about 10 pulses. In some embodiments, the number of voltage pulses to be administered is 3 voltage pulses. In other embodiments, a single voltage pulse is administered. In yet other embodiments, two voltage pulses are administered.

In some embodiments, the duration of each voltage pulse ("pulse width") ranges from about 1 msec to about 100 msec, e.g., about 5 msec, 10 msec, 15 msec, 25 msec, 50 msec, 60 msec, 75 msec, or another pulse width from about 1 msec to about 100 msec. In some embodiments, the pulse width is about 100 msec. In another embodiment, the pulse width is 10 msec. In another embodiment, the pulse width is 1 msec. In some embodiments, the square wave voltage pulses are administered on a 50% duty cycle.

In some embodiments, a single voltage pulse of −1.0 V with a width of 100 msec is administered.

In the transfection methods described herein, siRNA is transfected into the target population of cells using a transfection agent subsequent to voltage-preconditioning of the cells. In various embodiments, the transfection agent and siRNA are added to the cells within about ten minutes following voltage pre-conditioning of the cells as described herein. In some embodiments, the transfection agent and siRNA are present in the pre-conditioning buffer during the voltage pre-conditioning step. In other embodiments, the transfection agent and siRNA are added to the cells in pre-conditioning period about 30 seconds to about 10 minutes following the voltage-pre-conditioning, e.g., about 1 minute, 2 minutes, 3 minutes, 5 minutes, 6.5 minutes, 7 minutes or another interval from about 30 seconds to about 10 minutes following the voltage pre-conditioning step.

Following addition of the siRNA and transfection agent to the cells in pre-conditioning buffer, the cells to be transfected are incubated for a period of about 1 minute to about 20 minutes, e.g., about 5 minutes, 7 minutes, 10 minutes, 15 minutes, or another incubation period from about 1 minute to about 20 minutes.

After the siRNA/transfection incubation period the pre-conditioning buffer containing the siRNA and transfection reagent is replaced with a suitable cell culture medium, and cell culture is continued until the desired time point, typically at least about 30 minutes to about 48 hours following transfection, e.g., about 40 minutes, 1 hours, 2 hours, 3 hours, 4 hours, 8 hours, 12 hours, 16 hours, 20 hours, 30 hours, 36 hours, or another time period from at least about 30 minutes to about 48 hours following transfection.

A number of devices are suitable for administering voltage pulses according to the method described herein. In some embodiments, the device to be used is a voltage pulse generator, e.g., the Pragmatic 2414A waveform generator (Pragmatic Instruments, Inc., San Diego). In other embodiments, the device to be used is an electroporator equipped with a module suited for low voltage pulse delivery, and control of voltage pulse width.

In some embodiments, the transfection agent is a polycationic transfection agent such as polyethyleneimine. In one embodiment, the transfection agent is M.W. 25,000 (Dalton) branched polyethyleneimine. Other suitable transfection agents include, but are not limited to, Lipofectamine 2000®; Fugene®, linear PEI; N4'-(2,3-dioleyloxy)propylJ-N,N,N-trimethylammonium chloride (DOTMA), N-[1-(2,3-Dioleoyloxy)propyl]-N,N,N-trimethylammonium methyl-sulfate (DOTAP), poly-L-lysine, peptide-enhanced cationic lipids, or a combination thereof.

In some embodiments, nucleic acids other than siRNAs (e.g., miRNAs) may also be transfected using the methods described herein insofar the ratio of nucleic acid to PEI falls within the range of about 15-30 and that the PEI-nucleic acid complexes formed are in the range of 100-150 nm in diameter.

PEI/siRNA complexes are pre-formed, in some cases, by mixing PEI/siRNA at a ratio of about 30 in deionized water for about 20 minutes to about 30 minutes at room temperature prior to addition to cells.

III. COMPOSITIONS

Also described herein are compositions relating to high efficiency transfection of siRNA.

Such compositions include, for example, kits for implementing the methods described herein. In some embodiments, a high efficiency siRNA transfection kit will include one or more cell culture vessels configured with an electrically conductive cell culture surface (e.g., a surface containing indium tin oxide) suitable for voltage pre-conditioning of cells to be grown in the cell culture vessels as described herein, and, in addition, a transfection agent suitable for siRNA transfection by the methods described herein. In some embodiments of the kit, PEI is the transfection agent that is included. Suitable cell culture vessel formats include, but are not limited to, 15 cm cell culture dishes, 10 cm cell culture plates, 35 mm cell culture plates, 96-well plates, 48-well plates, 24 well plates, 12 well plates, 384 well plates, 1536 well plates and the like. In some embodiments, the cell culture vessel is a 96 well plate, a 384 well plate or a 1536 well plate. In some embodiments, the one or more cell culture vessels have a glass bottom that is coated or layered with an electrically conductive cell culture surface layer.

In some embodiments, a cell culture vessel provided with the kit features at least one microelectrode array, comprising at least two to about 1,000 microelectrodes, e.g., about 5, 8, 10, 20, 60, 80, 100, 160, 200, 300, 400, 500, 600, 700, 800, 900, or another number of microelectrodes ranging from at least two to about 1,000 microelectrodes. In some embodiments, where multiple microelectrodes are provided, individual microelectrodes or subsets of electrodes can be controlled independently to provide a desired voltage pre-conditioning regimen.

Optionally, the kit may further include one or more siRNAs to be complexed with the included transfection agent for use in the transfection methods described herein. In some embodiments, the kit will also include, for added convenience, a population of adherent cells to be transfected growing on the electrically conductive cell culture surface within the one or more cell culture vessels.

Another composition useful for carrying out the high efficiency siRNA transfection methods described herein is a high efficiency siRNA transfection system that includes the following components: (i) a cell culture vessel containing cells cultured in a medium and adhering to an electrically conductive surface such as one that contains indium tin oxide; (ii) a voltage pulse generator coupled to the cell culture vessel; and (iii) a cationic transfection agent-siRNA complex within the cell culture vessel, where the transfection agent itself does not contain nanoparticles.

In some embodiments, the voltage pulse generator to be included is not capable of providing a voltage pulse beyond the range of about −10 V to about +10 V. In some cases, the cells included in the system are primary cells, e.g., neurons. In other cases, the cells included in the system are derived from a cell line such as the neuro2A cell line. Suitable cationic transfection agents for use in such systems include, but are not limited to, PEI.

Another composition disclosed herein includes transfection competent, voltage pre-conditioned cells, which are prepared by subjecting a population of cells to voltage pre-conditioning by the methods described herein. In some embodiments, the cells are quickly frozen (within about 10 minutes, e.g., about 30 seconds, 1 minutes, 2 minutes, 5 minutes, 7 minutes, or the like) in a suitable freezing medium and can be stored at low temperature, preferably about −60° C. or lower, e.g., about −80° C. Upon rapid thawing, the cells are then washed and resuspended in a pre-conditioning buffer containing an siRNA-transfection agent complex as described herein. After an incubation period not to exceed about 30 minutes, the cells are then pelleted and resuspended in a suitable cell cultured medium and plated for continued cell culture.

The invention will be more fully understood upon consideration of the following non-limiting Examples. It is specifically contemplated that the methods disclosed are suited for pluripotent stem cells generally. All papers and patents disclosed herein are hereby incorporated by reference as if set forth in their entirety.

EXAMPLES

Example 1

Experimental Procedures

Preparation of Cell Cultures in Indium Tin Oxide (ITO) Wells

ITO substrates were purchased from Delta Technologies with resistances 10-12/sq resistance (Delta technologies, Madison, Wis.). Glass wells (1 cm diameter) were attached to the substrates with polydimethyl siloxane (PDMS) (Sylgard 184, Dow Corning) polymer. Prior to cell seeding, the ITO based cell culture wells were thoroughly cleaned, and incubated with 1M sodium hydroxide for 15 min to remove organic residues. Next, the wells were thoroughly washed with distilled water for 6 times, dried and autoclaved for sterility. Neuro2a cells were seeded at 3,000 cells and grown at 37° C. for 24 hrs before transfection in 10% fetal bovine serum, penicillin/streptomycin (Lonza, Walkersville, Md., Catalog#09-757F) 1% antibiotics, advanced MEM media (catalog#12492-Gibco, Life technologies). Primary hippocampal neurons (E18 mice) were purchased from (Brainbits, Llc, Springfield, Ill.) and seeded at 3,000-5,000 cells per well. The cells were allowed to grow and differentiate till DIV 4 prior to transfection.

Voltage-Controlled siRNA Transfection

For siRNA transfection, ALEXA FLUO® 555 conjugated negative control siRNA (Qiagen) with target sequence (5'-CAGGGTATCGACGATTACAAA-31ALEXA FLUO® 555) SEQ ID NO:1) and GAPDH siRNA (Qiagen) with target sequence (5'-CCGAGCCACATCGCTCAGACA-3' SEQ ID NO:2) was used. 25K branched polyethyleneimine was bought from Sigma Aldrich (CAS#9002-98-6). PEI/siRNA nanocomplexes with N/P ratios of 30 were mixed in deionized water and incubated for 20-30 min at room temperature. Cells were prepared by washing two times with PBS and filled with 300 μl of PBS without calcium or magnesium. Using a voltage pulse generator (Pragmatic 2414A waveform generator, San Diego, Calif.) cells were exposed to square wave pulse trains (n=1 to 10) with a 50% duty cycle in the range of ±3V. Pulse widths were varied from 1 ms, 10 ms, and 100 ms. Optimal pulse trains used bursts of n=3 cycles. Immediately after exposure to various voltages, the cells were incubated with preformed complexes of PEI/siRNA for 10 min. After the exposure, PBS was aspirated and replaced with media. Live assays were performed by 20 min incubation with calcein AM (Anaspec, Fremont, Calif.). DAPI (invitrogen) was used for imaging cell nuclei in some experiments. Image acquisition was done 4-8 hrs after transfection using appropriate filters and a LEICA® DFC345Fx monochromatic camera with advanced fluorescence suite.

Image Analysis

For live assay, percentage transfection was calculated in n=4 images and calculated as the ratio of number of cells with siRNA fluorescence (ex555) regardless of specific loading intensity and the number of calcein AM (ex488) stained cells. For DAPI based assays, images were acquired using two different filters and superimposed using ImageJ (NIH). Transfection efficiencies were calculated in n=4 images as the ratio of number of cells with siRNA fluorescence surrounding a nucleus divided by the number of stained nuclei. Each DAPI stained nuclei was counted as one cell. For live and DAPI based assays, the cells were counted and analyzed using ImageJ (NIH).

Image acquisition utilized same acquisition time and settings to accurately capture the fluorescence intensity changes due to modulated siRNA loading within cells. The raw acquired images were imported to MATLAB and analyzed using the image processing toolbox. For whole image analysis, the intensity distribution was plotted using boxplots and compared to background samples 10 background samples were collected for each image and pre-condition and typically represented areas with no cells. The intensity level on background samples corresponding to the upper whisker on the boxplot (representing 1.5 times the difference between the 25% percentile marker and the 75% percentile marker) was taken as the threshold for positive signal. Therefore, the threshold was defined as:

$$T = Q1 + 1.5(Q1 - Q3), \quad (1)$$

Where T is threshold value, Q1 is the 25% percentile marker for all data points, and Q3 is the 75% percentile marker for all data points. Outliers were defined as points beyond the whisker endpoints. In a Gaussian plot, this point would represent 92% of a normal distribution. Similar threshold markers were used for single cell analyses. Pixels in an image or cell with intensities above the threshold were considered as positive signal and pixels below as background. To assess the siRNA loading quantitatively, boxplots of signal distribution after background subtraction were used to calculate the number of pixels above background. To assess level of siRNA (FIG. 5c) the proportion of signal pixels above background to total number of pixels in individual cell images grabs were assessed for n=20 cells per pre-condition. For intensity weighted number of pixels (FIG. 6b & FIG. 6c), the individual pixel intensities for each cell was weighted by the number of pixels above background and then normalized to the total number of pixels in each cell image grab.

For immunocytochemistry studies with GAPDH siRNA, Quantitative values for pixel based fluorescent intensity values were generated using ImageJ. Typical pixel intensity distributions in a cell for each pre-condition is plotted in FIG. 7b. Background subtraction for each image of cells with threshold criteria as in equation 1 was used. A positive signal was a pixel with intensity value above the threshold criteria. The intensity weighted number of fluorescent pixels after background subtraction for each image and pre-condition was normalized to the cell count in each image and plotted in FIG. 8

Example 2

Figure 2:
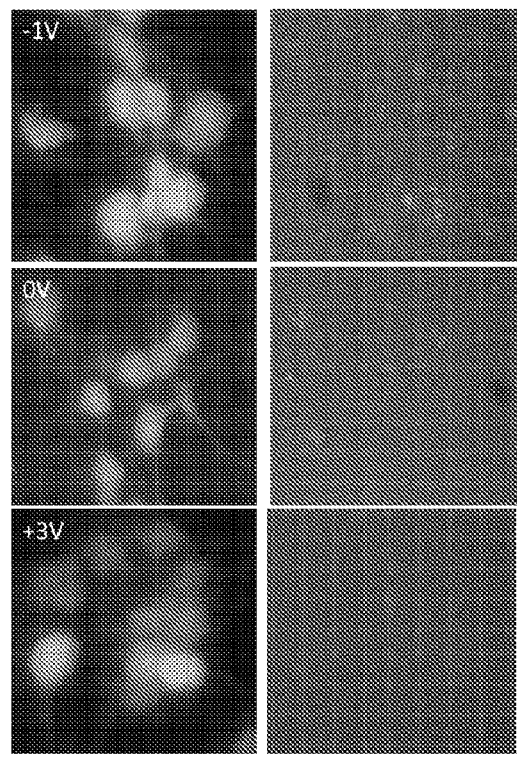
FIG. 2 Panel (A) A standard live assay (left) using calcein-AM (Anaspec) in siRNA-transfected primary neurons transfected derived from E18 mice (Brainbits, LLC) and having been preconditioned at various voltages at DIV 4 (days in vitro). Panel (B) shows a bar graph depicting transfection efficiencies for the above-mentioned experiment. Transfection efficiencies were 30%±18% (0V) (n=125 cells), 76%±10% (−1V) (n=59 cells), and 3%±3% (+3V) (n=67 cells). Efficiencies were assessed over n=4 images of neurons imaged for caleinAM (live assay) and ALEXA FLUOR® 555 conjugated siRNA for each preconditioning voltage using ImageJ software. Bar indicates 50 µm.
Figure 2:
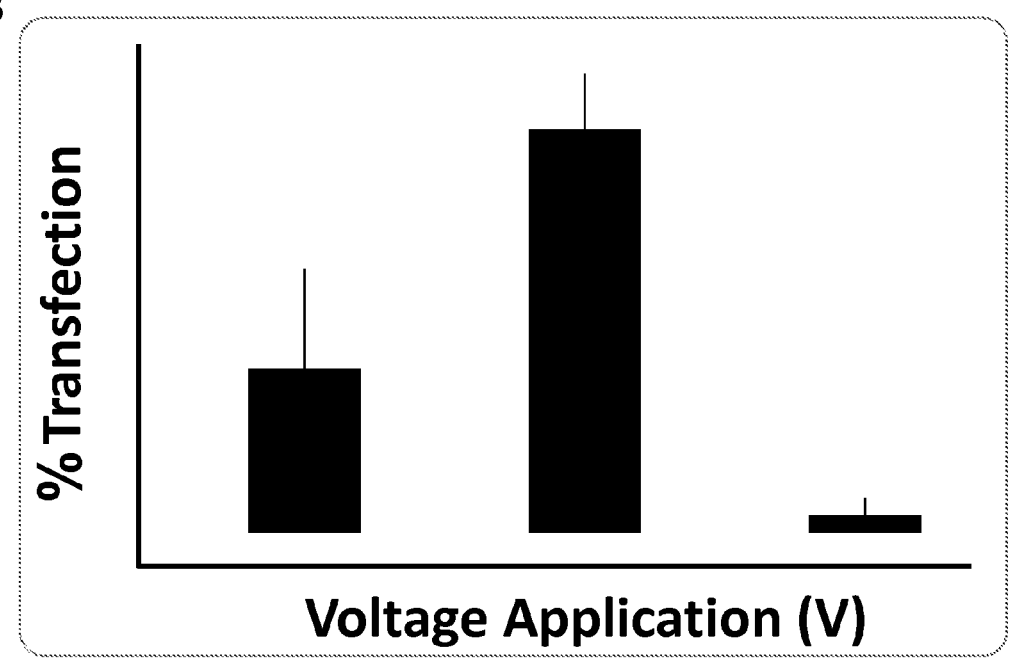

PEI-siRNA Transfection Efficiency is Enhanced with Voltage Pre-Conditioning of Target Cells Fluorescently tagged siRNA was complexed with PEI and administered to neuro2a cells that were preconditioned at different voltages. A live cell assay was performed on transfected cells 8 hours after the application of ±1 V, ±3 V, and 0 V (FIG. 1). When no voltage (0 V) was applied to the cells, siRNA transfection efficiencies were 62%±14% in live cells. There was a significant increase in siRNA transfection efficiencies to 98%±3.8% after the application and removal of −1 V. After pre-conditioning the cells at 3 V, 37%±7.5% of the live cells were visibly transfected, however with much less fluorescent intensity in the transfected cells compared to those after pre-conditioning at −1 V. Similar modulation trends were also observed in siRNA loading in primary hippocampal neurons. In primary hippocampal neurons (DIV 4) transfection efficiency with PEI/siRNA complexes was 76%±10% assessed 18 hrs after pre-conditioning with −1 V compared to 30%±18% with no pre-conditioning (0 V) as shown in FIG. 2. Virtually no fluorescently tagged siRNA was observed to enter neurons preconditioned at +3 V. Images of primary neurons that were preconditioned showed no difference in morphology compared to the non-preconditioned neurons (data not shown).

Figure 3:
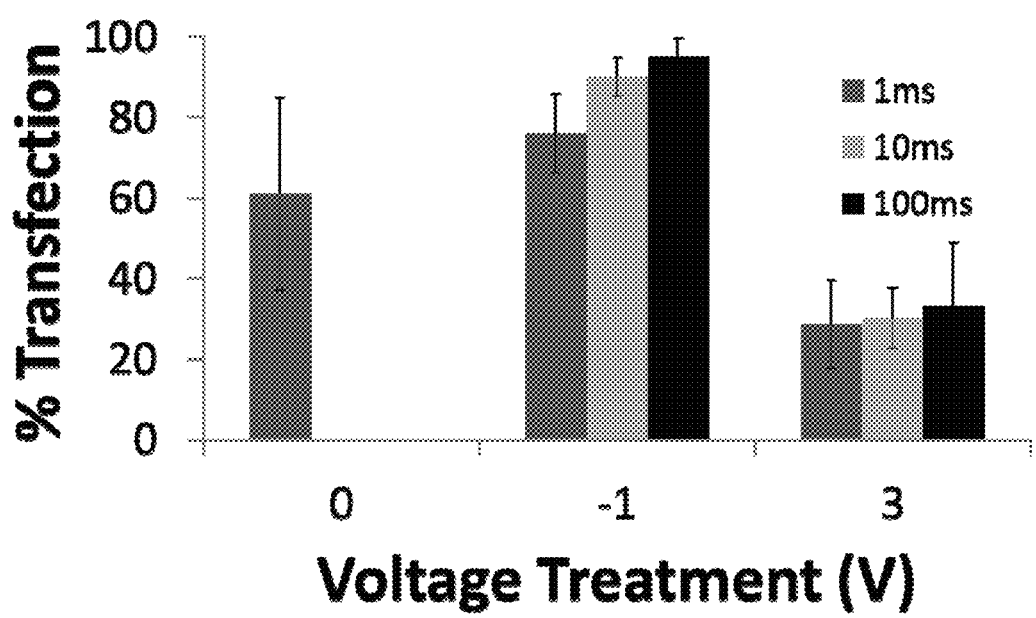
FIG. 3 Comparison of transfection efficiencies of ALEXA FLUOR® 555 conjugated control siRNA under different pulse width conditions (1 ms, 10 ms, 100 ms). Transfection efficiency was assessed using superimposed images of neuro2a cells using ImageJ with DAPI nuclear stain and transfected siRNA. Transfection efficiencies were calculated based on the ratio of cells with fluorescently tagged siRNA to total nuclei present in n=4 images after 0 V (no voltage), −1 V, and +3 V voltage preconditioning. Transfection efficiencies at 0 V were variable (61%±24%). At −1 V, transfection efficiencies were 76%±9.9% (1 ms pulse width), 90%±4.9% (10 ms pulse width) and 95%±4.5% (100 ms pulse width). At +3 V, transfection efficiencies were 29%±11% (1 ms pulse width), 30%±7.6% (10 ms pulse width) and 33%±16% (100 ms pulse width).

In separate experiments, fluorescently tagged siRNA were loaded in PEI complexes, transfected into neuro2a cells at different pulse widths and were subsequently imaged using DAPI nuclear stain (FIG. 3). Transfection efficiencies at 10 ms pulse width at different voltages were found to be comparable to those determined using the live assay in the earlier experiments, where a 10 ms pulse width was also used (FIG. 3). Transfection efficiencies were significantly lower (~29-33%) after pre-conditioning the cells with voltage pulses at +3 V and different pulse widths compared to 0 V (~61%). On the other hand, after pre-conditioning at −1 V, the transfection efficiencies were marginally lower (76%±9.9%) at a pulse width of 1 ms compared to efficiencies of 90%±4.9% for a pulse width of 10 ms and 95%±4.5% for a pulse width of 100 ms. No significant changes in transfection efficiencies were observed after the application and removal of +3 V at different pulse widths (1-100 ms).

Modulated siRNA Loading within Individual Cells

Figure 4:
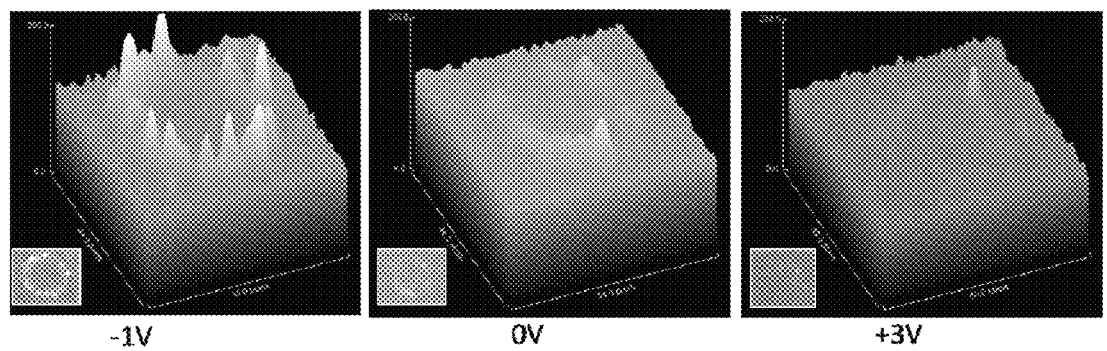
FIG. 4 Representative single cell comparison of fluorescent intensity distributions of voltage modulated transfection of ALEXA FLUOR® 555 conjugated control siRNA at 10 ms pulse width. Individual cells (based on the nuclei stained images) were evaluated for the distribution of red pixels after preconditioning at 0 V, −1 V, +3 V and transfection of ALEXA FLUOR® 555 conjugated control siRNA. Pixel intensity information was derived from ImageJ and assessed for siRNA loading. Cells treated with −1 V had more loading overall compared to transfected cells in +3 V. Insets show representative cells with siRNA transfection.
Figure 12:
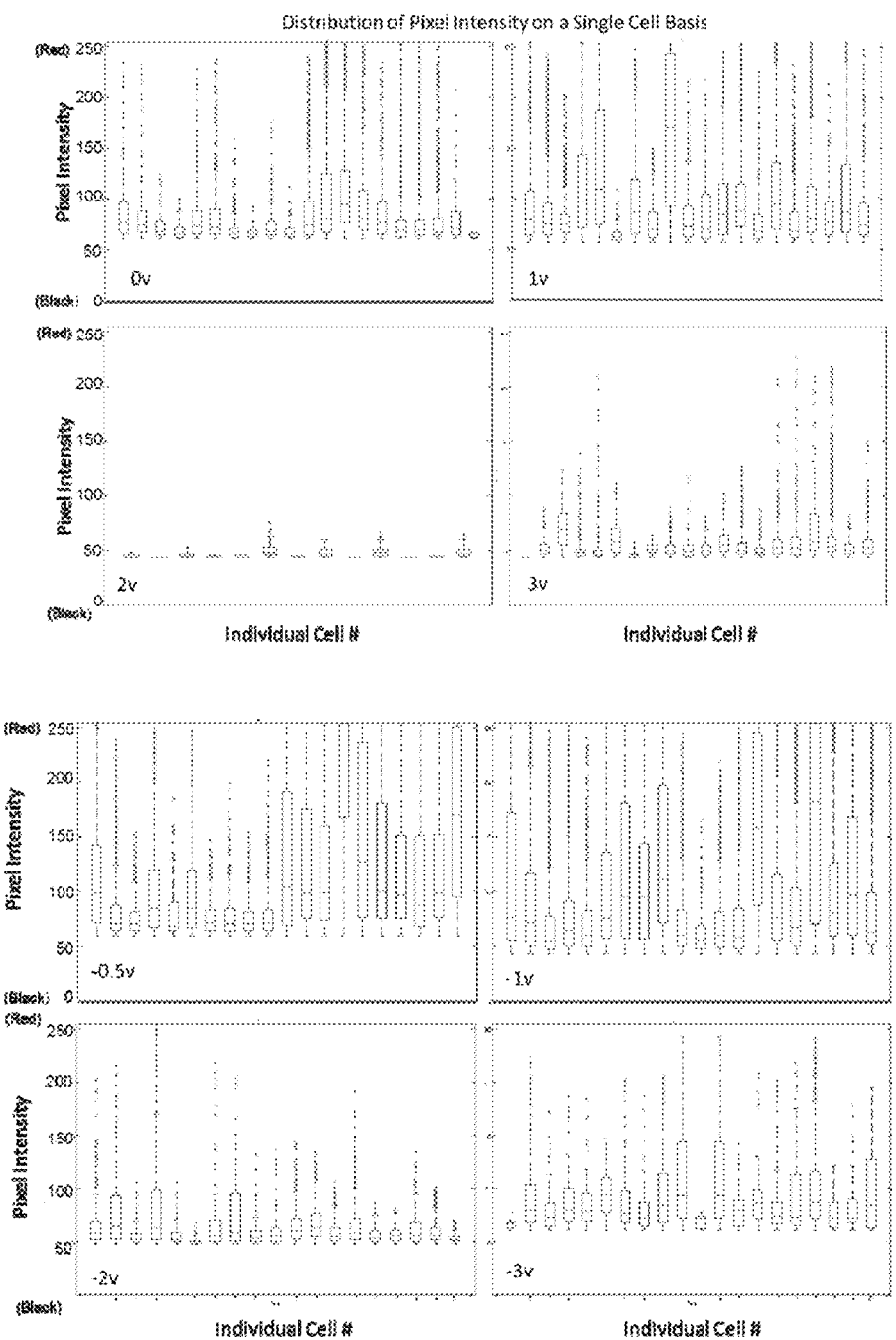
FIG. 12 Intensity distribution in individual cells (n=20) for each voltage application. Cells transfected with fluorescent siRNA were evaluated for the intensity distribution of red pixels in the range of ±3 V. Pixel intensity information was derived using the image processing toolbox in MATLAB and plotted in boxplots with background subtraction. The distribution of red pixels is indicative of siRNA loading in individual cells. The end whisker points on the boxplot represent 1.5 times the width of the difference between the 75% and 25% quartile markers.

In cells that were successfully transfected, there were variations in the level of siRNA loaded as indicated by pixel intensity distributions within individual cells (FIG. 12). The intensity distribution for 20 randomly picked cells for the case of PEI only transfection conditions (corresponding to 0 V controls) had lower median and inter-quartile distance than those corresponding to −0.5 V or −1 V conditions. Cells pre-conditioned with ±2-3 V conditions had much lower median values and a narrower distribution of pixel intensities than compared to those cells pre-conditioned between ±1V. The presence of pixels with high intensities is indicative of higher density of siRNA in a given space within a cell. The intracellular, spatial distribution of siRNA in live cells was more uniform after pre-conditioning with −1 V compared to the distribution in cells preconditioned at other voltages (FIG. 1). Cells preconditioned with +3 V had distinguishable, intense spots of fluorescence inside the cell suggesting isolated, localized endocytosis of siRNA. Much lower siRNA uptake was also observed in transfected cells after pre-conditioning with +3 V compared to transfected cells after pre-conditioning with −1V. The fluorescent siRNA intensity distribution of representative transfected cells at each voltage level was individually analyzed as surface plots (FIG. 4). Since fluorescently tagged, negative control siRNA cannot enter the nucleus, the fluorescent intensity distribution was mainly located in the cytosol surrounding the nucleus. The relative change in pixel intensity from the center of the cell to the outer edge after pre-conditioning at −1 V was ~80 relative fluorescence units (RFUs), 40 RFUs for 0 V, and negligible variation at +3 V. For the cells preconditioned with +3 V, asymmetric distribution of siRNA was observed with small highly intense, concentrated points that were ~50 RFUs.

Figure 5:
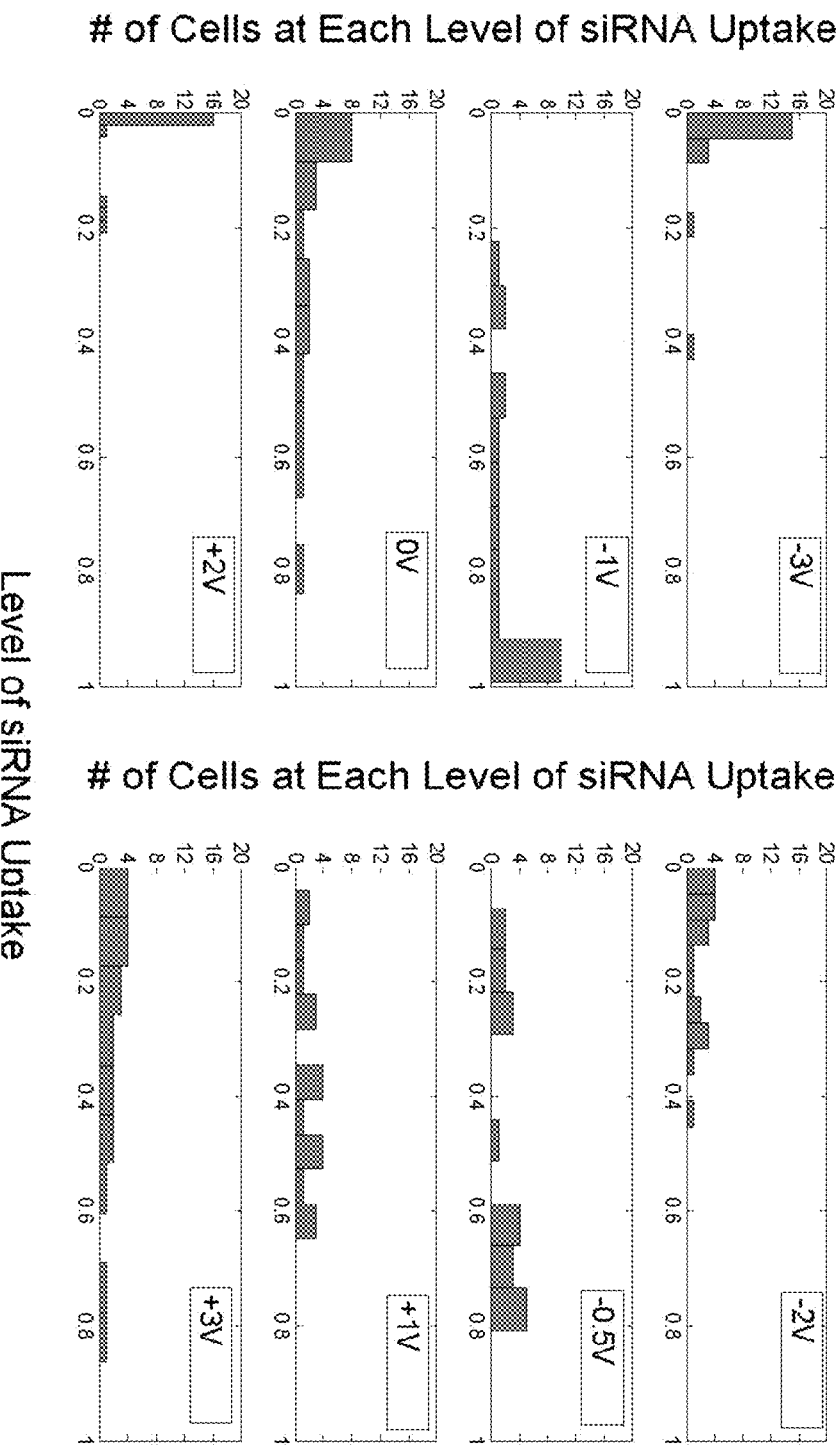
FIG. 5 shows a series of bar graphs illustrating the distribution of siRNA uptake levels in neuro2a cells under various voltage pre-conditioning conditions. Using image analysis, the level of siRNA loading in n=20 cells for each preconditioning voltage was determined by the proportion of the sum of red pixels after background subtraction for each cell normalized to the total number of pixels for an individual cell image. The distribution of cells at each level of siRNA loading (0-1 on x-axis) was plotted for each pre-conditioning voltage (±3V). SiRNA loading in cells with no preconditioning (0V) were significantly lower compared to siRNA loading at −1V. The general trend of decreasing siRNA loading was observed from −1V (peak levels) to marginal levels (±2-3V). Proportionally decreasing changes in siRNA uptake from −1V to +1V to +2-3V were found to be significant. ($p<0.0001$)
Figure 6:
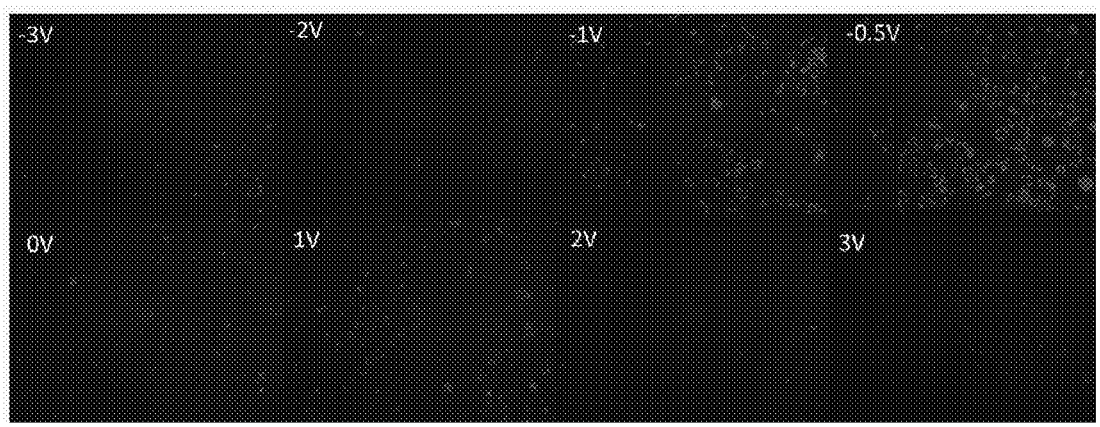
FIG. 6 shows fluorescence images of dosage dependent siRNA loading in neuro2a cells. Cells were preconditioned with different voltages at 10 ms pulse width (A) and a sample of n=20 cells pooled from multiple images were assessed for the total number of red pixels using MATLAB image processing tool-box.

FIG. 5 shows the individual variations in siRNA uptake in 20 different cells for each pre-conditioning voltage. The level of siRNA uptake was measured as the proportion of fluorescent pixels to the total number of pixels for an individual cell, with low levels corresponding to low uptake and high levels corresponding to high siRNA loading. The level of siRNA uptake within transfected cells preconditioned at −1 V showed higher levels of siRNA loading compared to transfected cells at 0V (no pre-conditioning). In addition, the level of siRNA uptake among the cells was modulated from increasing to decreasing levels from −1 V to +3 V, respectively. For pre-conditioning voltages less than −1V, a dramatic decrease in siRNA uptake is observed. High variations in siRNA uptake among individual cells is seen at 0 V (no-preconditioning) with 40% of the measured cells showing only marginal siRNA uptake. Nevertheless, the trend of voltage-modulated siRNA loading is observed despite moderate variations in siRNA uptake among pre-conditioned transfected cells were observed among the pre-conditioned cells, Example 3

Figure 7:
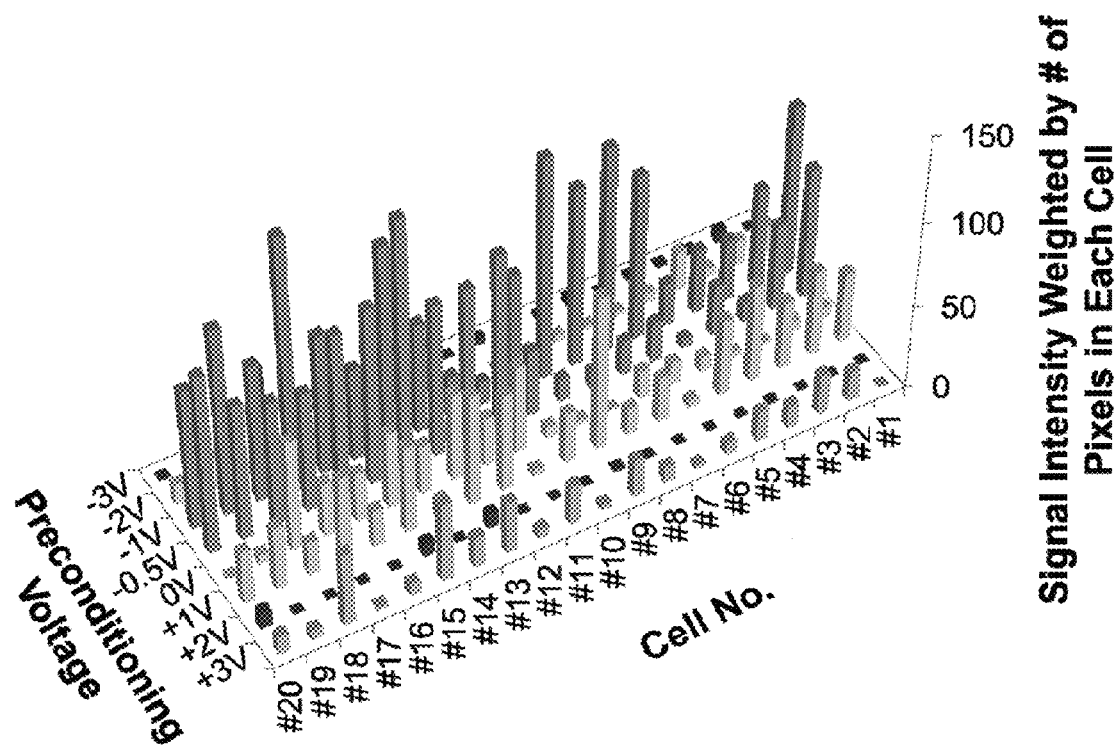
FIG. 7 shows a series of bar graphs of fluorescent signal intensity within each individual cell from the experiment described in FIG. 6. The relative amount of siRNA uptake is shown. To obtain a quantitative measure of siRNA uptake, each pixel intensity was weighted by the sum of red pixels after background subtraction and adjusted to the total number of pixels for an individual cell image. Pre-conditioning voltage dependent siRNA loading in individual cells is observed.
Figure 8:
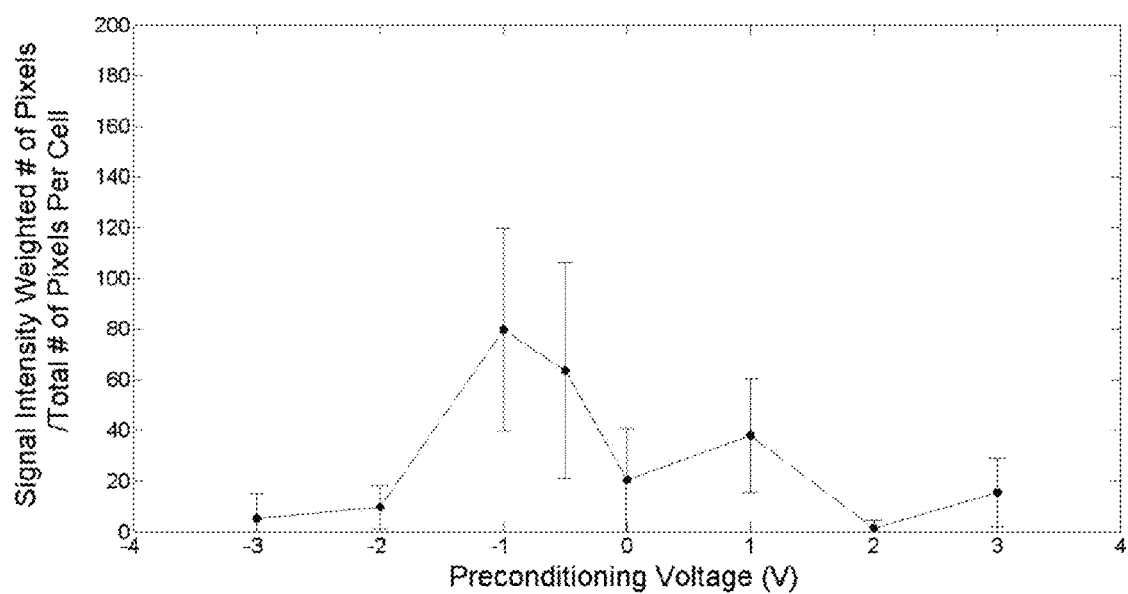
FIG. 8 shows a line graph illustrating the average signal intensity weighted distribution from (n=20 cells for each pre-conditioning voltage used in the experiment described in FIG. 6) for determining siRNA uptake levels at each pre-conditioning voltage is shown. siRNA loading was highest at −1 V pre-conditioning and lowest at ±2-3V An inverse relationship was observed between the siRNA uptake and increasing electric field intensity. Statistical analyses of means between −1V and +1V, ±2V, ±3V gave $p<0.0001$, suggesting a voltage-dependent modulated uptake of siRNA.
Figure 13:
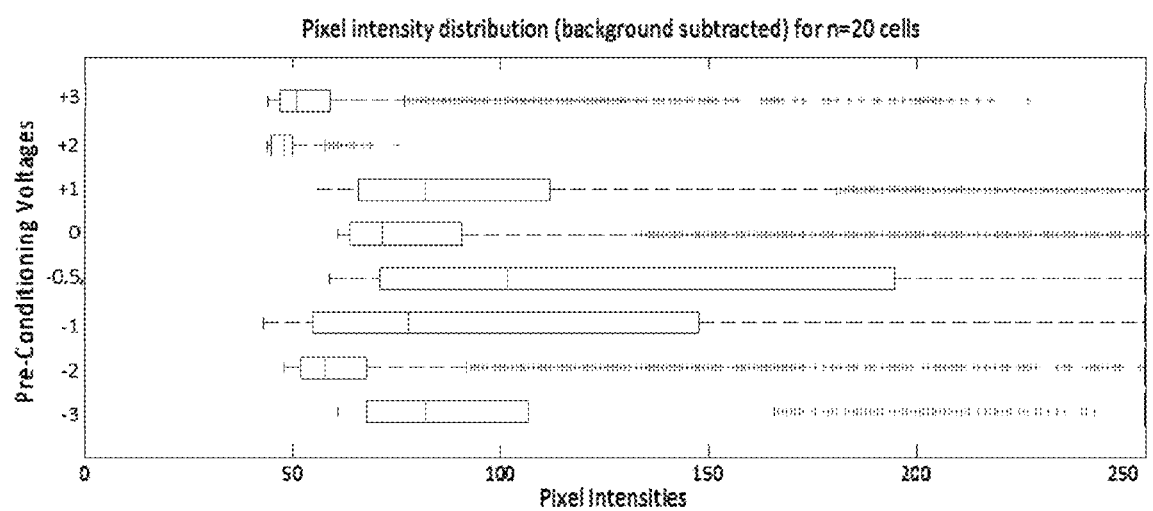
FIG. 13 Combined Intensity distribution (n=20) for each voltage application. Cells transfected with fluorescent siRNA were evaluated for the intensity distribution of red pixels for voltages in the range of ±3 V. Pixel intensity information was derived using the image processing toolbox in MATLAB and plotted in boxplots after background subtraction. The median intensity value for each voltage application was used to weight the total of number of red pixels in each cell for plots in FIG. 4.

Determination of the Optimal Pre-Conditioning Voltage and Level of Modulated siRNA Uptake in Cells To accurately quantify the level of siRNA loading, neuro2a cells were loaded with fluorescent siRNA using voltage pre-conditioning, imaged without additional contrast stains, and analyzed for pixel population distribution over different intensities using MATLAB (FIG. 6). siRNA loading in cells was quantified for the voltage range of ±3V (eight different voltage levels). The total sum of red pixels (direct measure of siRNA loading in cells) was highest for marginally negative voltage treatments (−1V and −0.5V) and lowest for voltages greater than ±2V, suggesting a voltage dependent siRNA loading. Analysis of intensity weighted sum of all red pixels above background for 20 randomly chosen cells from each voltage application (total 160 cells) also suggested a voltage dependent loading in cells (FIG. 7). Detailed analysis of the intensity distribution plots for each of the transfected cells for each pre-conditioning voltage tested is shown in FIG. 12. The pixel intensity distribution of all 20 cells at each of the eight pre-conditioning voltages tested is shown in FIG. 13. Finally, the red pixels in FIG. 13 are weighted by their corresponding intensities to get an intensity weighted count of red pixels (as a measure of siRNA loading in cells) and is plotted against the corresponding pre-conditioning voltage in FIG. 8. A relative change of ~3-4 fold in cell loading was observed when cells were pre-conditioned with voltages between −1 V and 0 V compared to those pre-conditioned with 1 V (FIG. 8). It should be noted that even at voltages that inhibited transfection of PEI-siRNA complex (i.e. have transfection efficiencies lower than observed with PEI transfection alone) there is some low level of siRNA loading above background as observed at +1-3V. Therefore, voltage pre-conditioning of cells modulated siRNA loading within transfected cells with less loading occurring at higher voltages (e.g., +3V) and higher loading occurring at around −1V suggesting a controllable voltage-dependent siRNA loading phenomenon for small populations of cells.

Example 4

Voltage-Dependent, Functional Silencing of GAPDH

Figure 9:
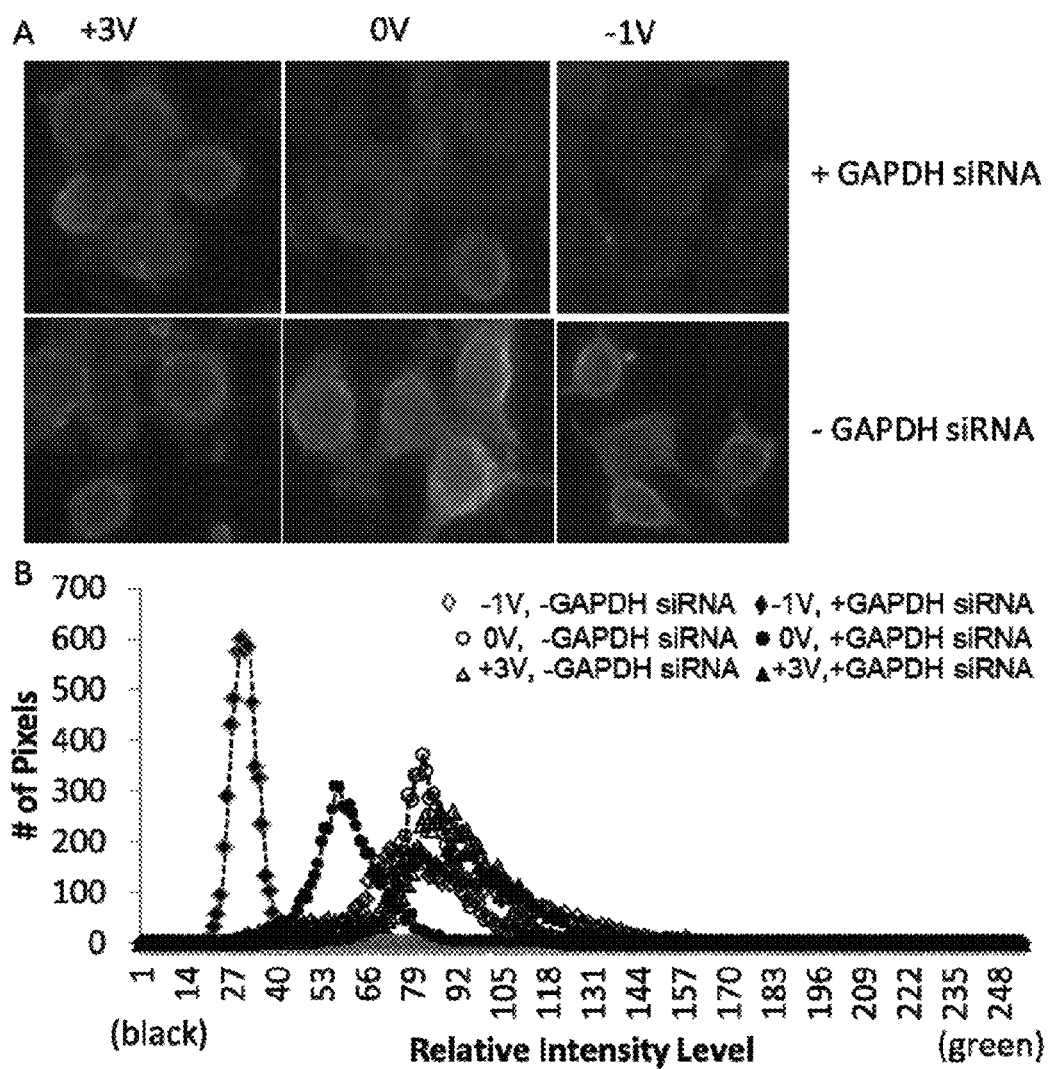
FIG. 9 Protein expression analysis of GAPDH siRNA treated neuro2a cells eight hours post transfection. (A) Representative fluorescence images of cells treated at +3 V, 0 V, and −1 V in the presence or absence of GAPDH siRNA. (B) Representative individual cell intensity histograms at various voltages. Filled symbols represent treatment with GAPDH siRNA at different voltages, while unfilled points represent voltage treatment of cells without GAPDH siRNA. Diamonds correspond to −1 V treatment, circles correspond to 0 V treatment, and triangles correspond to +3V treatment. Differential siRNA loading with voltage application in cells allows for modulated expression of GAPDH in cells.

Using GAPDH siRNA we were able to show a voltage-dependent functional silencing in neuro2a cells using the voltage-preconditioning method (FIG. 9a). Immunocytochemistry of cells with antibodies against GAPDH gene shows partial silencing of GAPDH in cells 8 hours after transfection. A histogram analyzing the intensity distribution of pixels in representative individual cells after pre-conditioning at different voltages shows a large number of pixels at high intensity corresponding to endogenous levels of GAPDH and significantly smaller number of pixels at high intensities corresponding to preconditioning at 0 V and −1 V (FIG. 9b). It is expected that as siRNA loading increases, the number of fluorescent pixels corresponding to GAPDH level would decrease due to siRNA induced inhibition. The result here suggests that the differences in siRNA loading levels at the individual cell level contributed to the modulated expression of GAPDH. Cells preconditioned with +3 V and transfected with GAPDH siRNA showed no significant difference in GAPDH levels compared with endogenous GAPDH levels in controls.

Figure 10:
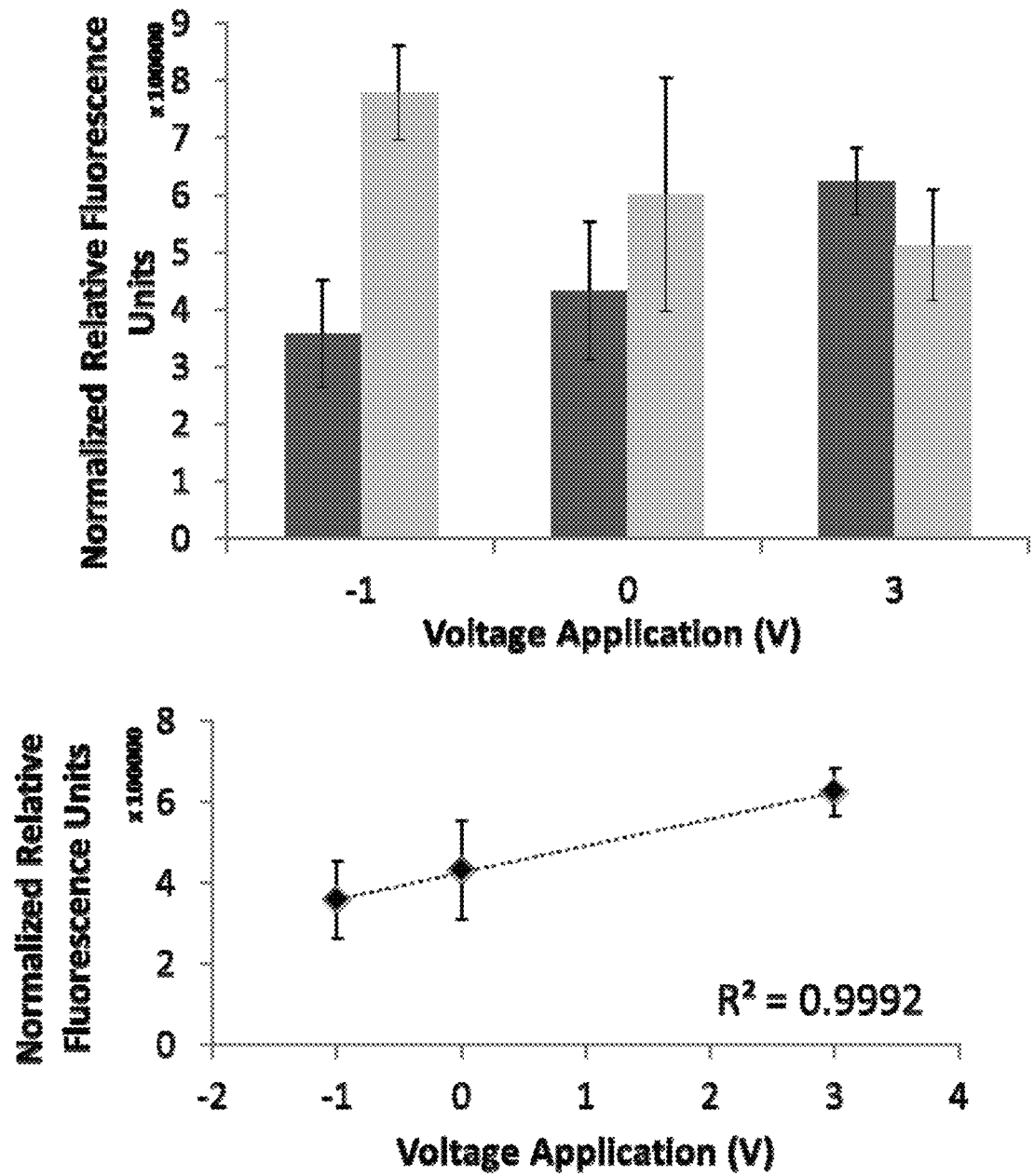
FIG. 10 Voltage dependent silencing of GAPDH in Neuro2a cells. GAPDH expression was assessed using fluorescently tagged antibodies of GAPDH siRNA. (A) Fluorescence was quantitatively assessed using intensity weighted sum of pixels normalized to cell count in n=3 independent experiments. Dark gray represents samples treated with GAPDH siRNA and light gray represents samples without GAPDH siRNA. (B) Linear regression of GAPDH expression shows a high degree of correlation between the level of pre-conditioning voltage and level of GAPDH expression. There is ~2-fold difference between +3V treated cells as compared to −1V treated cells.
Figure 11:
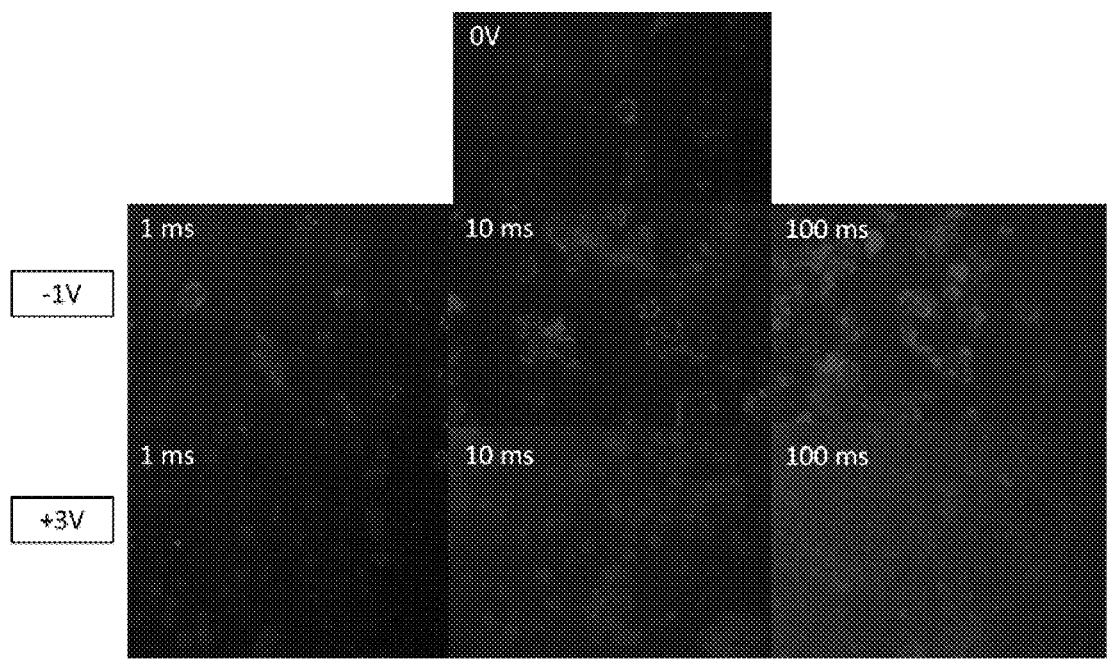
FIG. 11 Representative fluorescence images of voltage modulated transfection of ALEXA FLUOR® 555 conjugated negative control siRNA under different pulse width conditions. Cells were incubated with 200 nM fluorescently labeled siRNA-PEI complex for 10 min in all conditions. DAPI nuclear stain was used to identify all cells adhered on the surface. Images were taken at 20X using a LEICA® camera and superimposed using ImagaJ. Transfection efficiencies were calculated as the ratio of cells with fluorescently tagged siRNA to total nuclei present in n=4 images for 0 V, −1 V, and +3 V voltage applications.

For larger sample sizes (~150 cells per pre-condition), quantification of overall GAPDH expression levels in multiple cells from n=3 independent experiments shows an approximately 2-fold increase in the level of GAPDH expression between pre-conditioning at −1 V and +3 V and GAPDH siRNA (FIG. 10, upper panel). A highly correlative response between siRNA loading and functional silencing is seen (FIG. 10, lower panel)). Endogenous expression levels of GAPDH do not change significantly in control experiments with voltage application without GAPDH siRNA.

In this study, we demonstrated an efficient transfection approach that combines voltage pre-conditioning approach with a chemical transfection technique that can be readily modified and possibly complement current high throughput technologies for difficult-to-transfect cells such as adherent neuro2a cells and primary neurons.

This hybrid technique is rapid, consistent, repeatable and scalable to high-throughput applications. In contrast to many other transfection methods, cell viability is virtually unaffected by the reported technique. In addition, analysis of the GAPDH expression levels in voltage-preconditioned cells in control experiments suggests endogeneous levels are not affected by voltage pre-conditioning. In comparison to typical PEI based transfection of siRNA, voltage controlled PEI/siRNA complex delivery showed (a) less variability and (b) rapid assimilation of siRNA in cells with (c) higher efficiency. Control chemically based transfection with PEI yielded high variability in transfection efficiency (±24%) The observed level of siRNA loading in voltage preconditioned cells had less variability in transfection efficiencies when compared with the case when only PEI-siRNA complex is used (without voltage pre-conditioning), which showed large differences in siRNA concentrations in individual, transfected cells. PEI based transfection of siRNA in literature is known for notoriously low levels of transfection in difficult-to transfect cells like primary neurons as demonstrated in our current study without any pre-conditioning voltage. For primary neurons, the observed transfection efficiency using only PEI and no pre-conditioning was significantly lower than the corresponding values for neuro2a cells possibly due to the level of differentiation and relative cell size. High levels of siRNA loading could be achieved using the voltage-preconditioning method for both neuro2a and primary hippocampal neurons in culture, suggesting a broader application of the technique across multiple neuron-like cell types.

Figure 14:
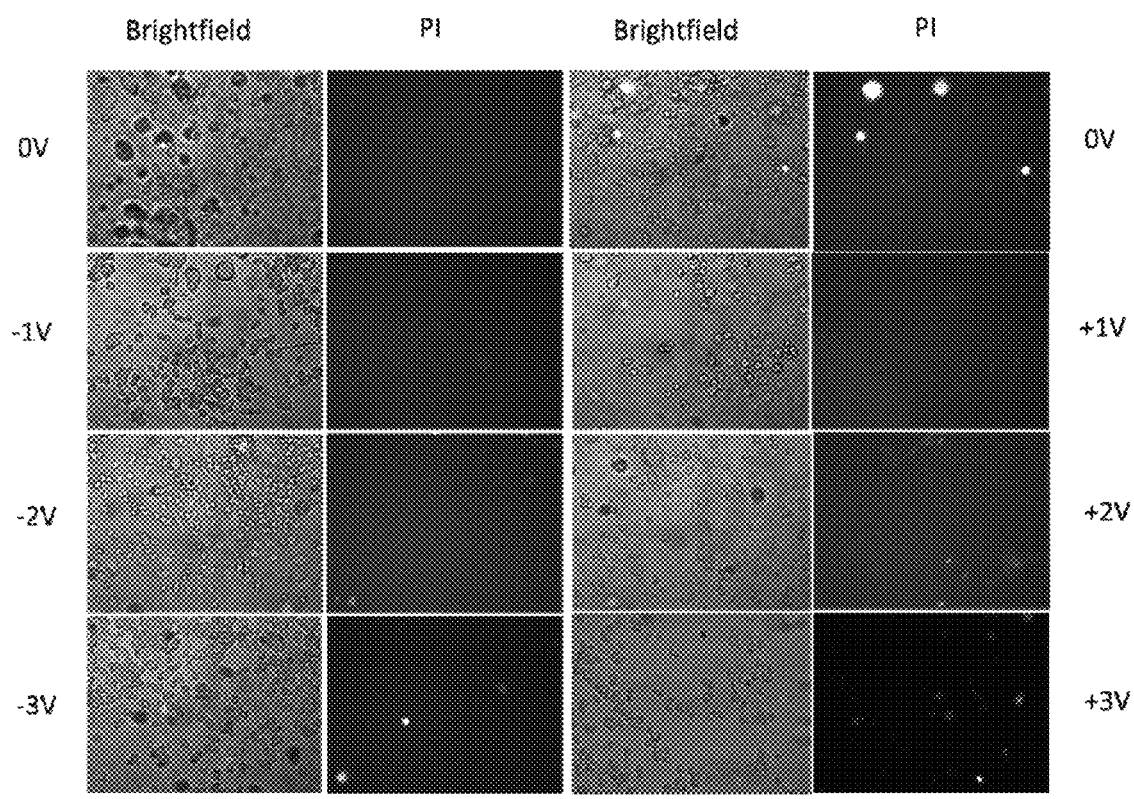
FIG. 14 Propidium Iodide (PI) Uptake in Voltage Preconditioned Cells. Cells were preconditioned at various voltages (±3 V) with PI in the PBS buffer to assess diffusion due to pore formation. No significant enhancement in PI uptake is seen, suggesting electroporation is not a plausible mechanism for the modulated uptake observed in this study.

In the above-described studies, electroporation and membrane breakdown is not expected as a mechanism of siRNA transfer due to low electric field strengths (<30 V/cm). For electroporative gene transfer a minimum of 0.3 kV/cm is typically necessary for transfection. In contrast, COMSOLTM simulations (results not shown) of the pre-conditioning transfection methods described here indicate that electric field intensities are at least 1-2 orders below the range typically required for electroporation. In addition, experiments involving voltage-preconditioned cells with propidium iodide dye, a classic marker to study diffusion due to electroporative pore formation, showrf no cellular uptake at −1 V (FIG. 14). Further experiments are needed to better understand the synergistic contributions of electrokinetic attraction and the electroendocytic pathway. Nevertheless, it is clear that a manipulation of the cell surface using voltage preconditioning is necessary for modulating the delivery of PEI-siRNA complexes.

GAPDH typically has high expression in a cell and relevant in the energy metabolism in neurons and neuron-like cells and therefore commonly used as a housekeeping gene control in experiments. We saw proportional, partial knockdown in GAPDH expression for a given stock concentration of siRNA 8 hrs after transfection, which is consistent with previous reports in literature. Up to 2-fold changes in GAPDH expression levels were demonstrated due to silencing. The level of gene silencing is however expected to be dependent on the level of corresponding endogenous gene expression in cells at any given time. The functional effect could be more dramatic in genes that have lower expression levels and the preconditioning protocol presented in this paper needs to optimized for specific genes and cell type. Alternate means of optimizing and controlling siRNA loading can be achieved by varying exposure time, point of application, and variation in voltage pulse numbers.

Example 5

Voltage-Dependent siRNA Dosing and Functional Silencing of BDNF

Brain derived neurotrophic factor (BDNF) siRNA (Santa Cruz Biotechnologies) was transfected, using voltage pre-conditioning under various voltage pulsing regimens, into primary hippocampal neurons (4 DIV), cultured for 24 hours before being fixed and immunostained for MAP-2 (microtubule associated protein-2), which is specific to dendrites of neurons. Voltage pre-conditioning allows differential uptake of BDNF siRNA. As shown in FIG. 15, compared to controls, the number and length of neurite extensions in BDNF siRNA-treated cells were lower as more siRNA uptake occurred under −1V and 0V transfections, as compared to the +3 V pre-conditioning transfection. The cells pre-conditioned with +3V were also affected but to a lesser extent than cells with 0V or −1V pre-conditioning, suggesting that a low-level of siRNA uptake occurred. Also, a cytotoxic effect of enhanced BDNF siRNA uptake was also seen with increased uptake. At −1V a lower cell density was seen, while at +3V similar cell densities are maintained compared to controls. The data suggested that controlled, programmable uptake of siRNA can be achieved by systematically varying pre-conditioning voltage pulse parameters, which result in dose-dependent functional effects in cells.

Example 6

Location-Addressable Transfection Using Voltage Pre-Conditioning Using a Microelectrode Array Platform We explored the potential to adopt the voltage pre-conditioning method to high-throughput applications, e.g., siRNA library phenotypic screening. To this end, voltage pre-conditioning and transfection was carried out by culturing primary hippocampal neurons on an ITO based microelectrode array with 100 µm diameter transparent electrodes. Neurons were grown on the electrodes until 12 DIV and then transfected with a combination of siRNAs (ALEXA FLUOR® 555 conjugated negative controls+Bace1 siRNA). As shown in FIG. 16(A), location-addressable, modulated siRNA uptake was demonstrated on an array of 9 different electrodes: three using −1V pulses, three using 0V pulses, and three using +3V pulses. Increased uptake is seen in −1V electrodes compared to 0V and +3V similar to the macroscale methods previously described. (B) Here the electrophysiological functional effect of BACE1 siRNA transfection is shown. Electrophysiological data was taken 1 hour post transfection. The average spike rate (# of action potentials) per sec increases >45% for −1V and 0V in ⅚ electrodes. The one electrode with cells pre-conditioned with −1V had a negative change in spike rate possibly due to neuronal network dynamics. Nevertheless, the magnitude of change exceeds >63%. The average spike rate for the cells pre-conditioned with +3V is only a modest change indicating low level uptake cells. The data here suggest (a) the pre-conditioning method can be scaled down to micron scale for use in microelectrode arrays and (b) modulated functional effects of neurons can be measured at micron scales.

In conclusion, the voltage-modulated siRNA cell loading method we have described has successfully combined the major advantages of rapid delivery and tunability afforded by the use of an electrical field in combination with chemical transfection techniques.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

What is claimed is:

1. A high efficiency short interfering RNA (siRNA) transfection method comprising:
   (i) subjecting a population of cells adhering on an electrically conductive cell culture surface to one or more low voltage pulses to condition the cells for chemical transfection without causing the formation of pores; and
   (ii) transfecting siRNA, using a chemical transfection agent, into the electrically conditioned population of cells, following the one or more low voltage pulses to obtain a transfected population of viable cells, wherein the one or more low voltage pulses provide a voltage from about −3 V to about +3 V.

2. The method of claim 1, wherein the population of cells comprises primary cells.

3. The method of claim 1, where the electrically conductive cell culture surface comprises indium tin oxide.

4. The method of claim 1, wherein the population of adhering cells is less than 80% confluent during the transfection step.

5. The method of claim 1, where the one or more low voltage pulses comprises three low voltage pulses.

6. The method of claim 1, wherein the electrically conductive cell culture surface is provided in the form of one or more microelectrodes.

7. The method of claim 1, wherein the electrically conductive cell culture surface is provided in the form of two or more microelectrodes.

8. The method of claim 7, wherein the electrically conductive cell culture surface is provided as a microelectrode array.

9. The method of claim 7, wherein the one or more low voltage pulses may be a negative voltage pulse or a positive voltage pulse.

10. The method of claim 1, wherein the one or more low voltage pulses provide a voltage of about −1 V.

11. The method of claim 1, wherein the one or more low voltage pulses has a width of about 1 msec to about 100 msec.

* * * * *